(12) United States Patent
Fanger et al.

(10) Patent No.: US 9,320,543 B2
(45) Date of Patent: Apr. 26, 2016

(54) POSTERIOR DYNAMIC STABILIZATION DEVICE HAVING A MOBILE ANCHOR

(75) Inventors: Jonathan Fanger, Raynham, MA (US); Missoum Moumene, Newton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 664 days.

(21) Appl. No.: 12/606,647

(22) Filed: Oct. 27, 2009

(65) Prior Publication Data

US 2010/0331886 A1    Dec. 30, 2010

Related U.S. Application Data

(60) Provisional application No. 61/220,341, filed on Jun. 25, 2009.

(51) Int. Cl.
*A61B 17/70* (2006.01)

(52) U.S. Cl.
CPC .......... *A61B 17/7008* (2013.01); *A61B 17/7005* (2013.01); *A61B 17/7035* (2013.01); *A61B 17/7037* (2013.01); *A61B 17/7046* (2013.01); *A61B 17/702* (2013.01)

(58) Field of Classification Search
CPC ........... A61B 17/7014; A61B 17/7008; A61B 17/7005
USPC ................................................ 606/250–267
See application file for complete search history.

(56) References Cited

U.S. PATENT DOCUMENTS

| | | |
|---|---|---|
| 3,992,725 A | 11/1976 | Homsy |
| 4,512,038 A | 4/1985 | Alexander |
| 4,648,388 A | 3/1987 | Steffee |
| 4,743,260 A | 5/1988 | Burton |
| 4,854,304 A | 8/1989 | Zielke |
| 5,002,542 A | 3/1991 | Frigg |
| 5,034,011 A | 7/1991 | Howland |
| 5,092,866 A | 3/1992 | Breard |
| 5,180,393 A | 1/1993 | Commarmond |
| 5,181,930 A | 1/1993 | Dumbleton |

(Continued)

FOREIGN PATENT DOCUMENTS

| | | |
|---|---|---|
| EP | 46518 | 7/1983 |
| EP | 470660 | 7/1995 |

(Continued)

OTHER PUBLICATIONS

Betz, "Compairson of Anterior and Posterior Instrumentation for Correction of Adolsecent Thoracic Idiipathic Scoliosis", SPINE, Feb. 1, 1999, vol. 24, Issue 3, pp. 225-239.

(Continued)

*Primary Examiner* — Ellen C Hammond
*Assistant Examiner* — Stuart S Bray (57) ABSTRACT

A posterior dynamic spinal stabilization device utilizing a spinal rod, a fixed anchor, a mobile anchor adapted for both translation and pivoting, a mobile anchor-limiting stop affixed to the rod and an optional bumper-type, a rod with at least one limiting stop. It allows predetermined and prescribed interpedicular motion. It allows the use of traditional pedicle screw-rod placement techniques in a flexible system possessing many treatment options using familiar components that are familiar to the surgeon, and can be used on multiple levels (especially to top off) and can transition loads by limiting displacements.

14 Claims, 8 Drawing Sheets

(56) References Cited

U.S. PATENT DOCUMENTS

| | | | |
|---|---|---|---|
| 5,207,678 A | 5/1993 | Harms | |
| 5,217,461 A | 6/1993 | Asher | |
| 5,217,497 A | 6/1993 | Mehdian | |
| 5,282,863 A | 2/1994 | Burton | |
| 5,344,422 A | 9/1994 | Frigg | |
| 5,360,431 A | 11/1994 | Puno | |
| 5,375,823 A * | 12/1994 | Navas | A61B 17/7005 267/153 |
| 5,387,213 A * | 2/1995 | Breard | A61B 17/7022 606/254 |
| 5,403,314 A | 4/1995 | Currier | |
| 5,415,661 A | 5/1995 | Holmes | |
| 5,423,816 A | 6/1995 | Lin | |
| 5,429,639 A | 7/1995 | Judet | |
| 5,437,669 A * | 8/1995 | Yuan | A61B 17/7047 606/264 |
| 5,474,555 A | 12/1995 | Puno | |
| 5,486,174 A | 1/1996 | Fournet Fayard | |
| 5,496,321 A | 3/1996 | Puno | |
| 5,520,689 A | 5/1996 | Schlapfer | |
| 5,540,688 A | 7/1996 | Navas | |
| 5,540,689 A | 7/1996 | Sanders | |
| 5,562,660 A | 10/1996 | Grob | |
| 5,562,663 A | 10/1996 | Wisnewski | |
| 5,562,737 A | 10/1996 | Graf | |
| 5,630,817 A | 5/1997 | Rokegem | |
| 5,643,260 A | 7/1997 | Doherty | |
| 5,658,286 A | 8/1997 | Sava | |
| 5,672,175 A * | 9/1997 | Martin | A61B 17/025 606/105 |
| 5,672,176 A | 9/1997 | Biedermann | |
| 5,683,390 A | 11/1997 | Metz Stavenhagen | |
| 5,702,395 A * | 12/1997 | Hopf | 606/250 |
| 5,704,936 A | 1/1998 | Mazel | |
| 5,704,937 A | 1/1998 | Martin | |
| 5,728,098 A | 3/1998 | Sherman | |
| 5,733,284 A | 3/1998 | Martin | |
| 5,738,685 A | 4/1998 | Halm | |
| 5,782,833 A * | 7/1998 | Haider | 606/266 |
| 5,797,910 A | 8/1998 | Martin | |
| 5,851,006 A | 12/1998 | Spillner | |
| 5,879,350 A | 3/1999 | Sherman | |
| RE36,221 E | 6/1999 | Breard | |
| 5,954,725 A | 9/1999 | Sherman | |
| 5,961,516 A | 10/1999 | Graf | |
| 6,004,349 A | 12/1999 | Jackson | |
| 6,022,350 A | 2/2000 | Ganem | |
| 6,053,917 A | 4/2000 | Sherman | |
| 6,063,090 A | 5/2000 | Schlapfer | |
| 6,077,262 A | 6/2000 | Schlapfer | |
| 6,083,226 A | 7/2000 | Fiz | |
| 6,099,528 A | 8/2000 | Saurat | |
| 6,102,912 A | 8/2000 | Cazin | |
| 6,139,549 A | 10/2000 | Keller | |
| 6,224,598 B1 | 5/2001 | Jackson | |
| 6,241,730 B1 | 6/2001 | Alby | |
| 6,248,105 B1 | 6/2001 | Schläpfer | |
| 6,251,112 B1 | 6/2001 | Jackson | |
| 6,267,764 B1 | 7/2001 | Elberg | |
| 6,273,888 B1 | 8/2001 | Justis | |
| 6,293,949 B1 | 9/2001 | Justis | |
| 6,302,888 B1 | 10/2001 | Mellinger | |
| 6,361,535 B2 | 3/2002 | Jackson | |
| 6,371,957 B1 | 4/2002 | Amrein | |
| 6,379,356 B1 | 4/2002 | Jackson | |
| 6,402,750 B1 | 6/2002 | Atkinson | |
| 6,402,752 B2 | 6/2002 | Schäffler Wachter | |
| 6,440,132 B1 | 8/2002 | Jackson | |
| 6,471,705 B1 | 10/2002 | Biedermann | |
| 6,485,491 B1 | 11/2002 | Farris | |
| 6,520,963 B1 | 2/2003 | McKinley | |
| 6,540,749 B2 | 4/2003 | Schäfer | |
| 6,554,831 B1 | 4/2003 | Rivard | |
| 6,595,993 B2 | 7/2003 | Donno | |
| 6,626,904 B1 * | 9/2003 | Jammet | A61B 17/7001 606/266 |
| 6,626,908 B2 | 9/2003 | Cooper | |
| 6,641,586 B2 | 11/2003 | Varieur | |
| 6,645,207 B2 | 11/2003 | Dixon | |
| 6,652,526 B1 | 11/2003 | Arafiles | |
| 6,695,843 B2 | 2/2004 | Biedermann | |
| 6,723,100 B2 | 4/2004 | Biedermann | |
| 6,726,687 B2 | 4/2004 | Jackson | |
| 6,730,089 B2 | 5/2004 | Jackson | |
| 6,755,829 B1 | 6/2004 | Bono | |
| 6,761,719 B2 | 7/2004 | Justis | |
| 6,770,075 B2 * | 8/2004 | Howland | A61B 17/7041 606/261 |
| 6,783,527 B2 | 8/2004 | Drewry | |
| 6,786,903 B2 | 9/2004 | Lin | |
| 6,796,984 B2 | 9/2004 | Soubeiran | |
| 6,835,205 B2 | 12/2004 | Atkinson | |
| 6,843,791 B2 | 1/2005 | Serhan | |
| 6,896,677 B1 | 5/2005 | Lin | |
| 6,905,500 B2 | 6/2005 | Jeon | |
| 6,918,911 B2 | 7/2005 | Biedermann | |
| 6,966,910 B2 | 11/2005 | Ritland | |
| 6,986,771 B2 | 1/2006 | Paul | |
| 6,989,011 B2 | 1/2006 | Paul | |
| 6,997,927 B2 | 2/2006 | Jackson | |
| 7,018,378 B2 | 3/2006 | Biedermann | |
| 7,022,122 B2 | 4/2006 | Amrein | |
| 7,029,475 B2 | 4/2006 | Panjabi | |
| 7,125,410 B2 | 10/2006 | Freudiger | |
| 7,137,985 B2 | 11/2006 | Jahng | |
| 7,156,850 B2 | 1/2007 | Kim | |
| 7,175,622 B2 | 2/2007 | Farris | |
| 7,179,261 B2 | 2/2007 | Sicvol | |
| 7,204,838 B2 | 4/2007 | Jackson | |
| 7,211,086 B2 | 5/2007 | Biedermann | |
| 7,261,714 B2 | 8/2007 | Richelsoph | |
| 7,326,210 B2 * | 2/2008 | Jahng et al. | 606/86 A |
| 7,329,258 B2 | 2/2008 | Studer | |
| 7,335,200 B2 | 2/2008 | Carli | |
| 7,419,714 B1 | 9/2008 | Magerl | |
| 7,553,320 B2 | 6/2009 | Molz, IV | |
| 7,556,639 B2 | 7/2009 | Rothman | |
| 7,621,912 B2 | 11/2009 | Harms | |
| 7,621,940 B2 | 11/2009 | Harms | |
| 7,632,292 B2 | 12/2009 | Sengupta | |
| 7,641,673 B2 | 1/2010 | Le Couedic | |
| 7,651,515 B2 | 1/2010 | Mack | |
| 7,708,762 B2 | 5/2010 | McCarthy | |
| 7,713,287 B2 | 5/2010 | Timm | |
| 7,717,941 B2 | 5/2010 | Petit | |
| 7,722,649 B2 | 5/2010 | Biedermann | |
| 7,727,258 B2 | 6/2010 | Graf | |
| 7,763,052 B2 | 7/2010 | Jahng | |
| 7,776,071 B2 | 8/2010 | Fortin | |
| 7,776,075 B2 | 8/2010 | Bruneau | |
| 7,794,476 B2 | 9/2010 | Wisnewski | |
| 7,811,309 B2 | 10/2010 | Timm | |
| 7,815,665 B2 | 10/2010 | Jahng | |
| 7,833,256 B2 | 11/2010 | Biedermann | |
| 7,846,187 B2 | 12/2010 | Jackson | |
| 7,862,586 B2 | 1/2011 | Malek | |
| 7,942,907 B2 * | 5/2011 | Richelsoph | 606/257 |
| 7,988,710 B2 | 8/2011 | Jahng | |
| 7,993,370 B2 | 8/2011 | Jahng | |
| 8,012,178 B2 | 9/2011 | Hartmann | |
| 8,157,843 B2 | 4/2012 | Biedermann | |
| 8,221,467 B2 | 7/2012 | Butler | |
| 8,221,472 B2 | 7/2012 | Peterson | |
| 8,241,362 B2 | 8/2012 | Voorhies | |
| 8,641,734 B2 | 2/2014 | Moumene | |
| 8,911,484 B2 | 12/2014 | Lei | |
| 8,974,497 B2 * | 3/2015 | Cho | A61B 17/702 606/254 |
| 2002/0058942 A1 | 5/2002 | Biedermann | |
| 2002/0072751 A1 | 6/2002 | Jackson | |
| 2002/0082602 A1 | 6/2002 | Biedermann | |
| 2002/0133155 A1 | 9/2002 | Ferree | |
| 2002/0133159 A1 | 9/2002 | Jackson | |

(56) References Cited

U.S. PATENT DOCUMENTS

| | | | |
|---|---|---|---|
| 2003/0009226 A1 | 1/2003 | Graf | |
| 2003/0041441 A1 | 3/2003 | Lin | |
| 2003/0055426 A1 | 3/2003 | Carbone | |
| 2003/0055427 A1 | 3/2003 | Graf | |
| 2003/0083657 A1 | 5/2003 | Drewry | |
| 2003/0100896 A1 | 5/2003 | Biedermann | |
| 2003/0109880 A1 | 6/2003 | Shirado | |
| 2003/0125741 A1 | 7/2003 | Biedermann | |
| 2003/0149431 A1 | 8/2003 | Varieur | |
| 2003/0153912 A1 | 8/2003 | Graf | |
| 2003/0171749 A1 | 9/2003 | Le Couedic | |
| 2003/0191470 A1 | 10/2003 | Ritland | |
| 2003/0220642 A1 | 11/2003 | Freudiger | |
| 2003/0220643 A1 | 11/2003 | Ferree | |
| 2004/0002708 A1 | 1/2004 | Ritland | |
| 2004/0049189 A1 | 3/2004 | Le Couedic | |
| 2004/0049190 A1* | 3/2004 | Biedermann et al. | 606/61 |
| 2004/0068258 A1 | 4/2004 | Schlapfer | |
| 2004/0073215 A1 | 4/2004 | Carli | |
| 2004/0097926 A1 | 5/2004 | Kim | |
| 2004/0097933 A1 | 5/2004 | Lourdel | |
| 2004/0106921 A1 | 6/2004 | Cheung | |
| 2004/0116927 A1 | 6/2004 | Graf | |
| 2004/0143264 A1 | 7/2004 | McAfee | |
| 2004/0167523 A1 | 8/2004 | Jackson | |
| 2004/0186474 A1 | 9/2004 | Matthis | |
| 2004/0186478 A1 | 9/2004 | Jackson | |
| 2004/0215191 A1 | 10/2004 | Kitchen | |
| 2004/0215192 A1 | 10/2004 | Justis | |
| 2004/0225289 A1 | 11/2004 | Biedermann | |
| 2004/0230191 A1 | 11/2004 | Frey | |
| 2004/0230192 A1 | 11/2004 | Graf | |
| 2004/0236327 A1 | 11/2004 | Paul | |
| 2004/0236328 A1 | 11/2004 | Paul | |
| 2004/0236329 A1 | 11/2004 | Panjabi | |
| 2004/0260284 A1 | 12/2004 | Parker | |
| 2004/0264386 A1 | 12/2004 | Ha | |
| 2004/0267260 A1 | 12/2004 | Mack | |
| 2005/0027292 A1 | 2/2005 | Bernard | |
| 2005/0033295 A1 | 2/2005 | Wisnewski | |
| 2005/0038432 A1 | 2/2005 | Shaolian | |
| 2005/0049708 A1 | 3/2005 | Atkinson | |
| 2005/0056979 A1 | 3/2005 | Studer | |
| 2005/0065514 A1 | 3/2005 | Studer | |
| 2005/0065516 A1 | 3/2005 | Jahng | |
| 2005/0080414 A1 | 4/2005 | Keyer | |
| 2005/0085814 A1 | 4/2005 | Sherman | |
| 2005/0085815 A1 | 4/2005 | Harms | |
| 2005/0101956 A1* | 5/2005 | Simonson | A61B 17/7007 606/279 |
| 2005/0113927 A1 | 5/2005 | Malek | |
| 2005/0124991 A1 | 6/2005 | Jahng | |
| 2005/0129499 A1 | 6/2005 | Morris | |
| 2005/0131407 A1 | 6/2005 | Sicvol | |
| 2005/0131421 A1 | 6/2005 | Anderson | |
| 2005/0131422 A1 | 6/2005 | Anderson | |
| 2005/0143737 A1 | 6/2005 | Pafford | |
| 2005/0143823 A1 | 6/2005 | Boyd | |
| 2005/0149020 A1 | 7/2005 | Jahng | |
| 2005/0154389 A1 | 7/2005 | Selover | |
| 2005/0154390 A1 | 7/2005 | Biedermann | |
| 2005/0165396 A1 | 7/2005 | Fortin | |
| 2005/0171543 A1* | 8/2005 | Timm | A61B 17/7007 606/257 |
| 2005/0177156 A1 | 8/2005 | Timm | |
| 2005/0177157 A1 | 8/2005 | Jahng | |
| 2005/0177164 A1 | 8/2005 | Walters | |
| 2005/0182400 A1 | 8/2005 | White | |
| 2005/0182401 A1 | 8/2005 | Timm | |
| 2005/0182409 A1 | 8/2005 | Callahan | |
| 2005/0187549 A1 | 8/2005 | Jackson | |
| 2005/0192589 A1 | 9/2005 | Raymond | |
| 2005/0202519 A1 | 9/2005 | Barthe | |
| 2005/0203511 A1 | 9/2005 | Wilson MacDonald | |
| 2005/0203513 A1 | 9/2005 | Jahng | |
| 2005/0203514 A1 | 9/2005 | Jahng | |
| 2005/0203516 A1 | 9/2005 | Biedermann | |
| 2005/0203517 A1 | 9/2005 | Jahng | |
| 2005/0203518 A1 | 9/2005 | Biedermann | |
| 2005/0203519 A1* | 9/2005 | Harms | A61B 17/7026 606/254 |
| 2005/0215999 A1 | 9/2005 | Birkmeyer | |
| 2005/0216003 A1 | 9/2005 | Biedermann | |
| 2005/0222569 A1* | 10/2005 | Panjabi | A61B 17/7028 606/257 |
| 2005/0222659 A1 | 10/2005 | Olsen | |
| 2005/0245930 A1 | 11/2005 | Timm | |
| 2005/0261685 A1 | 11/2005 | Fortin | |
| 2005/0261686 A1 | 11/2005 | Paul | |
| 2005/0267471 A1 | 12/2005 | Biedermann | |
| 2005/0277919 A1 | 12/2005 | Slivka | |
| 2005/0277922 A1* | 12/2005 | Trieu | A61B 17/7031 606/257 |
| 2005/0288670 A1 | 12/2005 | Panjabi | |
| 2005/0288672 A1 | 12/2005 | Ferree | |
| 2006/0009768 A1 | 1/2006 | Ritland | |
| 2006/0014259 A9 | 1/2006 | Burke | |
| 2006/0025767 A1 | 2/2006 | Khalili | |
| 2006/0036240 A1* | 2/2006 | Colleran | A61B 17/7025 606/86 A |
| 2006/0041259 A1 | 2/2006 | Paul | |
| 2006/0064090 A1 | 3/2006 | Park | |
| 2006/0084984 A1 | 4/2006 | Kim | |
| 2006/0106380 A1* | 5/2006 | Colleran et al. | 606/61 |
| 2006/0106381 A1 | 5/2006 | Ferree | |
| 2006/0129147 A1 | 6/2006 | Biedermann | |
| 2006/0142758 A1 | 6/2006 | Petit | |
| 2006/0142760 A1 | 6/2006 | McDonnell | |
| 2006/0149235 A1 | 7/2006 | Jackson | |
| 2006/0149291 A1 | 7/2006 | Selover | |
| 2006/0155279 A1* | 7/2006 | Ogilvie | A61B 17/6491 606/328 |
| 2006/0161152 A1 | 7/2006 | Ensign | |
| 2006/0184171 A1 | 8/2006 | Biedermann | |
| 2006/0189983 A1 | 8/2006 | Fallin | |
| 2006/0189984 A1* | 8/2006 | Fallin | A61B 17/7007 606/250 |
| 2006/0195093 A1 | 8/2006 | Jahng | |
| 2006/0201609 A1 | 9/2006 | Edwin | |
| 2006/0212033 A1* | 9/2006 | Rothman | A61B 17/7028 606/328 |
| 2006/0229607 A1* | 10/2006 | Brumfield | A61B 17/7002 606/264 |
| 2006/0229608 A1 | 10/2006 | Foster | |
| 2006/0229612 A1* | 10/2006 | Rothman | A61B 17/7074 606/279 |
| 2006/0240533 A1 | 10/2006 | Sengupta | |
| 2006/0247632 A1* | 11/2006 | Winslow | A61B 17/025 606/247 |
| 2006/0247637 A1* | 11/2006 | Colleran | A61B 17/7007 606/257 |
| 2006/0247638 A1 | 11/2006 | Trieu | |
| 2006/0260483 A1 | 11/2006 | Hartmann | |
| 2006/0264935 A1* | 11/2006 | White | A61B 17/7031 606/257 |
| 2006/0264937 A1* | 11/2006 | White | A61B 17/702 606/257 |
| 2006/0265074 A1* | 11/2006 | Krishna | A61B 17/7014 623/17.15 |
| 2006/0282080 A1 | 12/2006 | Albert | |
| 2007/0003598 A1 | 1/2007 | Trieu | |
| 2007/0005063 A1 | 1/2007 | Bruneau | |
| 2007/0016190 A1 | 1/2007 | Martinez | |
| 2007/0016201 A1 | 1/2007 | Freudiger | |
| 2007/0019808 A1 | 1/2007 | Gonzalez | |
| 2007/0049937 A1 | 3/2007 | Matthis | |
| 2007/0055241 A1 | 3/2007 | Matthis | |
| 2007/0055244 A1* | 3/2007 | Jackson | A61B 17/7028 606/86 A |
| 2007/0055247 A1 | 3/2007 | Jahng | |
| 2007/0161992 A1 | 7/2007 | Kwak | |
| 2007/0190230 A1 | 8/2007 | Trieu | |
| 2007/0191832 A1 | 8/2007 | Trieu | |
| 2007/0191841 A1* | 8/2007 | Justis et al. | 606/61 |

(56) References Cited

U.S. PATENT DOCUMENTS

| | | |
|---|---|---|
| 2007/0198088 A1 | 8/2007 | Biedermann |
| 2007/0233064 A1* | 10/2007 | Holt .................. A61B 17/7029 606/254 |
| 2007/0233073 A1 | 10/2007 | Wisnewski |
| 2007/0233085 A1 | 10/2007 | Biedermann |
| 2007/0233097 A1 | 10/2007 | Anderson |
| 2007/0270814 A1* | 11/2007 | Lim .................. A61B 17/7007 606/279 |
| 2007/0270838 A1* | 11/2007 | Bruneau ............ A61B 17/7031 606/250 |
| 2007/0270843 A1* | 11/2007 | Matthis ................ A61B 17/701 606/86 A |
| 2008/0021469 A1 | 1/2008 | Holt |
| 2008/0033435 A1 | 2/2008 | Studer |
| 2008/0058809 A1 | 3/2008 | Graf |
| 2008/0140133 A1* | 6/2008 | Allard .................. A61B 17/705 606/308 |
| 2008/0147122 A1* | 6/2008 | Jackson ........................ 606/246 |
| 2008/0161853 A1 | 7/2008 | Arnold |
| 2008/0161863 A1 | 7/2008 | Arnold |
| 2008/0183213 A1* | 7/2008 | Veldman .............. A61B 17/702 606/257 |
| 2008/0195105 A1 | 8/2008 | Sidebotham |
| 2008/0195153 A1* | 8/2008 | Thompson .................... 606/257 |
| 2008/0262552 A1 | 10/2008 | Kim |
| 2008/0312694 A1 | 12/2008 | Peterman |
| 2009/0005817 A1* | 1/2009 | Friedrich ........... A16B 17/7031 606/246 |
| 2009/0012562 A1 | 1/2009 | Hestad |
| 2009/0030464 A1 | 1/2009 | Hestad |
| 2009/0048631 A1* | 2/2009 | Bhatnagar .......... A61B 17/7004 606/246 |
| 2009/0062866 A1 | 3/2009 | Jackson |
| 2009/0099608 A1* | 4/2009 | Szczesny ........... A61B 17/7028 606/257 |
| 2009/0115289 A1 | 5/2009 | Asada |
| 2009/0131981 A1 | 5/2009 | White |
| 2009/0163953 A1 | 6/2009 | Biedermann |
| 2009/0163955 A1 | 6/2009 | Moumene |
| 2009/0204155 A1 | 8/2009 | Aschmann |
| 2009/0234388 A1 | 9/2009 | Patterson |
| 2009/0251573 A1 | 10/2009 | Toyoda |
| 2009/0326583 A1 | 12/2009 | Moumene |
| 2010/0010543 A1* | 1/2010 | Jackson ............... A61B 17/702 606/254 |
| 2010/0042156 A1 | 2/2010 | Harms |
| 2010/0069962 A1* | 3/2010 | Harms et al. .................. 606/254 |
| 2010/0069964 A1 | 3/2010 | Lechmann |
| 2010/0087863 A1* | 4/2010 | Biedermann ...... A61B 17/7029 606/261 |
| 2010/0114169 A1 | 5/2010 | Le Couedic |
| 2010/0114173 A1 | 5/2010 | Le Couedic |
| 2010/0174317 A1 | 7/2010 | Timm |
| 2010/0204736 A1 | 8/2010 | Biedermann |
| 2010/0274288 A1* | 10/2010 | Prevost ................ A61B 17/702 606/257 |
| 2010/0331886 A1 | 12/2010 | Fanger |
| 2011/0054534 A1 | 3/2011 | Biedermann |
| 2012/0265247 A1 | 10/2012 | Biedermann |
| 2014/0031868 A1 | 1/2014 | Biedermann |

FOREIGN PATENT DOCUMENTS

| | | |
|---|---|---|
| EP | 667127 | 8/1995 |
| EP | 677277 | 2/1996 |
| EP | 669109 | 5/1999 |
| EP | 1579816 | 6/2013 |
| FR | 2717370 | 9/1995 |
| GB | 2382307 | 5/2003 |
| WO | WO 9501132 | 1/1995 |
| WO | WO 9641582 | 12/1996 |
| WO | WO 0145576 | 6/2001 |
| WO | WO 0156489 | 8/2001 |
| WO | WO 03047441 | 6/2003 |
| WO | WO 2005027761 | 3/2005 |
| WO | WO 2005094704 | 10/2005 |
| WO | WO 2006079531 | 8/2006 |
| WO | WO 2006063107 | 12/2006 |

OTHER PUBLICATIONS

Nohara, "Biomechanical study of adjacent intervertebral motion after lumbar spinal fusion and flexible stabilization using polyethylene-terephthalate bands", J Spinal Discord Tech, Jun. 2004, vol. 17, Issue 3, pp. 215-219—abstract.

Poulin, "Biomechanical modeling of instrumentation for the scoliotic spine using flexible elements:a feasibility study", Ann Chir, 1998, 52(8), pp. 761-767—abstract.

Sanders, "A Preliminary Investigation of Shape Memory Alloys in the Surgical Correction of Scoliosis", SPINE, Sep. 15, 1999, vol. 18, Issue 12, pp. 1640-1646.

Smith, "Does Instrumented Anterior Scoliosis Surgery Lead to Pyphosis, Pseudarthrosis, or Inadequate Correction in Adults", SPINE, Mar. 1, 2002, vol. 27, Issue 5, pp. 529-534.

Teitelbaum, "New Percutaneously Inserted Spinal Fixation System", SPINE, Mar. 11, 2004, vol. 29, Issue 6, pp. 703-709.

Desroches "Biomechanical modeling of anterior spine instrumentation in AIS", Stud Health Technol Inform, 2006, vol. 123, pp. 415-418—abstract.

Veldhuizen, "A Scoliosis Correction Device Based on Memory Metal", Med. Eng. Phys., 1997, vol. 19, pp. 171-179, Elsevier Science Ltd.

Hefti, "Repair of lumbar spondylolysis with a hook-screw", Int Orthop., 1992, vol. 16, Issue 1, pp. 81-85—abstract.

* cited by examiner

POSTERIOR DYNAMIC STABILIZATION DEVICE HAVING A MOBILE ANCHOR

CONTINUING DATA

This patent application claims priority from pending U.S. Provisional Patent Application No. 61/220,341, filed Jun. 25, 2009, entitled "Posterior Dynamic Stabilization Device Having a Mobile Anchor" (DEP-6238USPSP), the specification of which is incorporated by reference in its entirety.

BACKGROUND OF THE INVENTION

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. Damaged, diseased levels in the spine were traditionally fused to one another. While such a technique may relieve pain, it effectively prevents motion between at least two vertebrae. As a result, additional stress may be applied to the adjoining levels, thereby potentially leading to further damage.

More recently, techniques have been developed to restore normal function to the facet joints. One such technique involves covering the facet joint with a cap to preserve the bony and articular structure. Capping techniques, however, are limited in use as they will not remove the source of the pain in osteoarthritic joints. Caps are also disadvantageous as they must be available in a variety of sizes and shapes to accommodate the wide variability in the anatomical morphology of the facets. Caps also have a tendency to loosen over time, potentially resulting in additional damage to the joint and/or the bone support structure containing the cap.

Other techniques for restoring the normal function to the posterior element involve arch replacement, in which superior and inferior prosthetic arches are implanted to extend across the vertebra typically between the spinous process. The arches can articulate relative to one another to replace the articulating function of the facet joints. One drawback of current articulating facet replacement devices, however, is that they require the facet joints to be resected. Moreover, alignment of the articulating surfaces with one another can be challenging.

Accordingly, there remains a need for improved systems and methods that are adapted to mimic the natural function of the facet joints.

Traditional spine fusion may result in early degeneration at adjacent spine levels due to increased loading and compensation. This may result in subsequent surgeries to fuse additional levels. Stabilization using more dynamic rods with traditional pedicle screw instrumentation may improve surgical outcomes and reduce additional surgeries for adjacent level degeneration.

PCT Patent Application WO02/17803 (Rivard I) and U.S. Pat. No. 6,554,831 (Rivard II) disclose a mobile dynamic implantable spinal apparatus designed with an aim towards treating scoliosis. Rivard I and II disclose a system including at least one correcting rod, at least one fixed bracket, at least one mobile carrier. The correcting rod is described as a scoliosis rod. Scoliosis rods are constructed of metallic materials, such as CoCr, Ti, and stainless steel. Such rods must be manufactured from very stiff materials in an effort to maintain correction.

U.S. Pat. No. 5,672,175 (Martin) discloses a dynamic spinal orthotic implant that preserves some of the physiologic spinal motion. The construct also includes a rod that is used to correct a lateral deviation or scoliosis curve.

US Patent Publication 2004/0049190 (Biedereman I) discloses a dynamic system utilizing two bone anchors, a rod, and a spring. One of the anchors is fixed to the rod, one anchor slides with respect to the rod, and the spring between them exerts a force from the fixed anchor to the sliding anchor.

US Patent Publication 2007/0233085 (Biedermann II) discloses a dynamic stabilization device utilizing a rod that is elastomeric and stretches rather than slides.

U.S. Pat. No. 7,326,210 (Jahng) discloses a dynamic stabilization device using a rod, elastomers, and a sliding sleeve.

SUMMARY OF THE INVENTION

The present invention relates to a posterior dynamic spinal stabilization device utilizing a spinal rod, a fixed anchor, a mobile anchor adapted for both translation and pivoting, a mobile anchor-limiting stop affixed to the rod and an optional bumper-type, a rod with at least one limiting stop.

In accordance with the present invention, there is provided a posterior dynamic spinal stabilization system comprising:
  a) a rod having a first end and a second end,
  b) a mobile anchor having i) a shank and ii) a rod-receiving portion mated to the first end of the rod, wherein the rod-receiving portion translates along the rod and pivots about the shank,
  c) a fixed anchor having i) a shank and ii) a rod-receiving portion locked to the second end of the rod.

The present invention provides a PDS device that allows predetermined and prescribed interpedicular motion. It is the understanding of the present inventor that this is the first PDS device of its kind to limit such motion by displacement of a mobile element (and not by load upon a static element). The PDS device of the present invention can also be made to be compatible with minimally invasive surgery (MIS) techniques. It allows the use of traditional pedicle screw-rod placement techniques in a flexible system, thereby enabling many different treatment options, using components that are familiar to the surgeon. The PDS device of the present invention intends to preserve desirable amounts of physiologic motion and can be used on multiple levels (especially to top off), to transition loads by limiting displacements.

The present invention contemplates a PDS device for motion applications. In this sense, it is different than certain motion devices used in scoliosis applications, such as those of Martin and Rivard, in which the device allows growth and limited motion along the longitudinal axis of the rod. Whereas Martin and Rivard contemplate a correcting scoliosis rod, the present invention contemplates mobile anchor PDS systems for treating stenosis, degenerative spondylolisthesis, and degenerative disc disease. In topping off applications, the present invention can be used as a protection device adjacent to a fusion to prevent overloading of the healthy discs. In some instances the device may be used at more than one level, thereby allowing the device to absorb some of the load and prevent adjacent disc disease.

Therefore, in accordance with the present invention, there is provided a method of treating a spine of a patient having iatrogenic instability, comprising the steps of:
 i) attaching to the spine a posterior dynamic spinal stabilization system comprising:
  a) a rod having a first end and a second end,
  b) a mobile anchor having i) a shank and ii) a rod-receiving portion mated to the first end of the rod, wherein the rod-receiving portion translates along the rod,
  c) a fixed anchor having i) a shank and ii) a rod-receiving portion locked to the second end of the rod,
 wherein the shank of the mobile anchor is attached to a first vertebra, and the shank of the fixed anchor is attached to the second vertebra.

The present invention allows desirable amounts of physiologic flexion, extension, lateral bending and axial rotation to be set by the surgeon after iatrogenic instability. The limited range of motion realized by the present invention is advantageous in certain PDS indications, such as topping-off fusions, stenosis, and degenerative spondylolisthesis.

Preferred embodiments of the present invention avoid the use of springs, and so allow motion to occur strictly within a desired window along the rod length. The extent of this limited motion is determined by a stop provided on the spinal rod component of the device, wherein the stop comprises a hard collar wrapped around the rod and an inferiorly-positioned soft bumper that prevents metal-on-metal contact between the anchor and the collar. Alternatively, a standard spinal rod having a conventional stop, furnished as either an integral or an attachable component, may be used.

One embodiment of the present invention allows the extent of anchor translation within the system to be dictated by the flexibility of the rod to which it is attached. The ability of the mobile anchor to slide on the rod will be dictated by the inherent flexibility of the rod. In these cases, a flexible rod will be expected to produce more translational motion, while a rigid rod would be expected to allow less translational motion.

The system of the present invention allows both the anchors and stops to be positioned at adjacent levels to limit motion, such that the loads can be effectively transitioned from one level to the next when topping off. This transitioning allows a motion gradient to be achieved to minimize overloads of adjacent levels. Because it beneficially provides physiologic displacements at adjacent levels, the present invention potentially beneficially reduces both the incidence of adjacent disc disease and the necessity of subsequent fusion procedures.

Although not necessarily preferred, the present invention may also utilize a spring rod or a polymer bumper to soften the flexion or extension limits. These soft stops would also allow motion similar to a neutral zone concept, wherein motion has relatively low resistance within the neutral zone but then experiences increased resistance after a prescribed limit.

Therefore, in accordance with the present invention, there is provided aposterior dynamic spinal stabilization system comprising:
 a) a rod having a first end and a second end,
 b) a mobile anchor having i) a shank and ii) a rod-receiving portion mated to the first end of the rod, wherein the rod-receiving portion translates along the rod,
 c) a fixed anchor having i) a shank and ii) a rod-receiving portion locked to the second end of the rod,
 d) a first motion-limiting stop positioned on the rod at a location superior to the mobile anchor, and
 e) a second motion-limiting stop positioned on the rod at a location inferior to the mobile anchor.

Also in accordance with the present invention, there is provided a posterior dynamic spinal stabilization system comprising:
 a) a rod having a first end and a second end,
 b) a mobile anchor having i) a shank and ii) a rod-receiving portion mated to the first end of the rod, wherein the rod-receiving portion translates along the rod,
 c) a fixed anchor having i) a shank and ii) a rod-receiving portion locked to the second end of the rod,
 d) a first motion-limiting stop positioned on the rod at a location inferior to the mobile anchor and comprising an elastic bumper.

Also in accordance with the present invention, there is provided a dynamic spinal stabilization system, comprising:
 a) a polyaxial head housing having a throughbore;
 b) a screw having a head and a shank, the shank passing through the throughbore of the housing;
 c) a locking cap adapted to apply axial pressure to screw head, thereby locking the shank with respect to a rod, the cap comprising a low friction, lower bearing surface for bearing upon the rod, and
 d) a set screw adapted to seat in the head housing to lock the rod thereto, the set screw comprising a low friction, upper bearing surface for bearing upon the rod.

DETAILED DESCRIPTION OF THE INVENTION

Figure 1A:
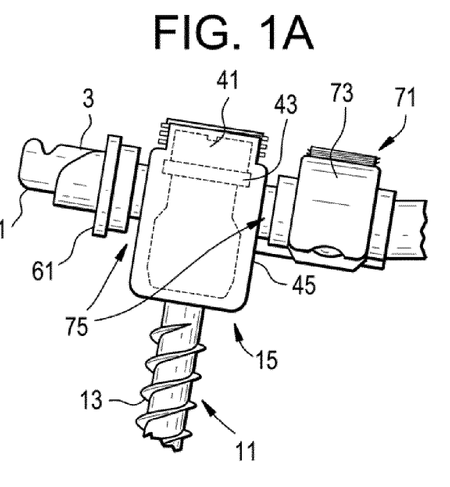
FIGS. 1a-1c disclose a posterior dynamic spinal stabilization system of the present invention.
Figure 1B:
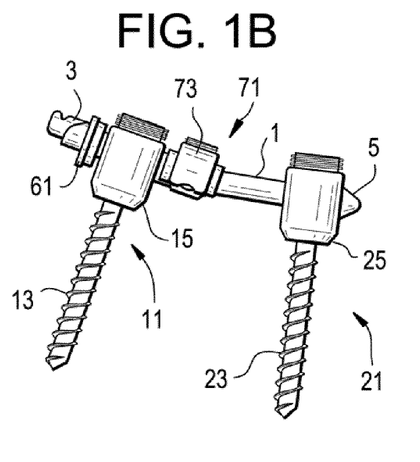
Figure 1C:
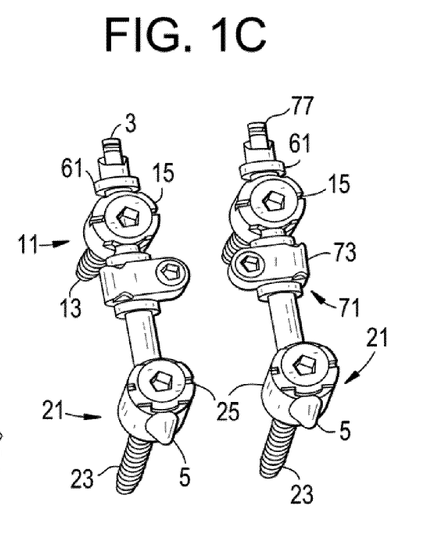
Figure 2:
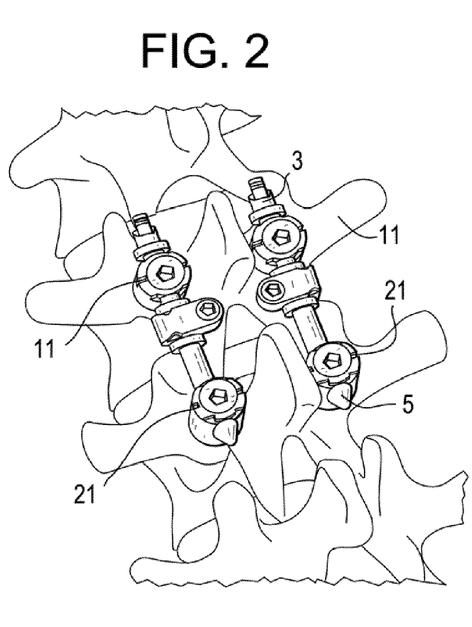
FIG. 2 discloses a posterior dynamic spinal stabilization system of the present invention implanted in a spinal column.

Now referring to FIGS. 1a-1c, in one preferred embodiment of the invention, there is provided a posterior dynamic spinal stabilization system, comprising:

a) a spinal rod 1 having a first end 3 used as a guide for a mobile anchor and a second end 5, b) a mobile anchor 11 having i) a shank 13 and ii) a rod-receiving portion 15 containing a bearing insert 45 (or "bearing") adapted to mate to the first end of the rod and the head of the shank, thereby enabling translation along the rod and pivoting about the rod, c) a fixed anchor 21 having i) a shank 23 and ii) a rod-receiving portion 25 adapted to lock to the second end of the rod.

d) a first motion-limiting stop 61 positioned on the rod at a location superior to the mobile anchor, and e) a second motion-limiting stop 71 positioned on the rod at a location inferior to the mobile anchor and comprising a polymeric bumper 73.

Now referring to FIG. 1*a*, gaps 75 are provided along the rod between the stops and the mobile anchor. The gaps define the extent of translation allowed to the mobile anchor. The length of each gap can be predetermined by the surgeon to limit translational anchor motion to a desired amount.

Polymer bearing insert 45 is shown through the polyaxial head in FIG. 1*a*. The low friction nature of the insert allows the bearing to pivot about the rod and allows the rod-receiving portion to translate. The polymeric nature of the insert also reduces friction between the anchor and rod, thereby promoting limited translational motion of the anchor along the rod.

Mobile anchors can allow translational motion, pivoting motion, or both motions, depending on the materials used in the insert and the type of set screw used. A pivoting mobile anchor that is allowed to only pivot can be transformed into one that both translates and pivots by providing a new set screw. Whereas the set screw for the pivot-only anchor would be a purely metallic set screw (which produces a high friction contact with the rod and thereby prevents translation), the set screw 41 for the pivot-plus-translate anchor would be a metal set screw with a polymer or other low friction rod-contacting surface 43 (which produces a low friction contact with the rod and thereby promotes limited translation).

In some embodiments of the present invention, the anchor is adapted to pivot by providing a bearing element 45 that surrounds the head of the shank and provides a surface to receive the rod. Preferably, the articulating face of this bearing element can be made of any material typically used in articulating prosthetic implants, such as metals, ceramics and polymers such as UHMWPE. Preferably, the articulating face has a low coefficient of friction.

In some embodiments, the mobile head component of the present invention is substantially similar to the mobile head components described in US Published Patent Application Nos. 2004/0225289 (Biedermann III); 2005/0203516 (Biedermann IV); and 2005/0277919 (Slivka), the specifications of which are incorporated by reference in their entireties.

Figure 3:
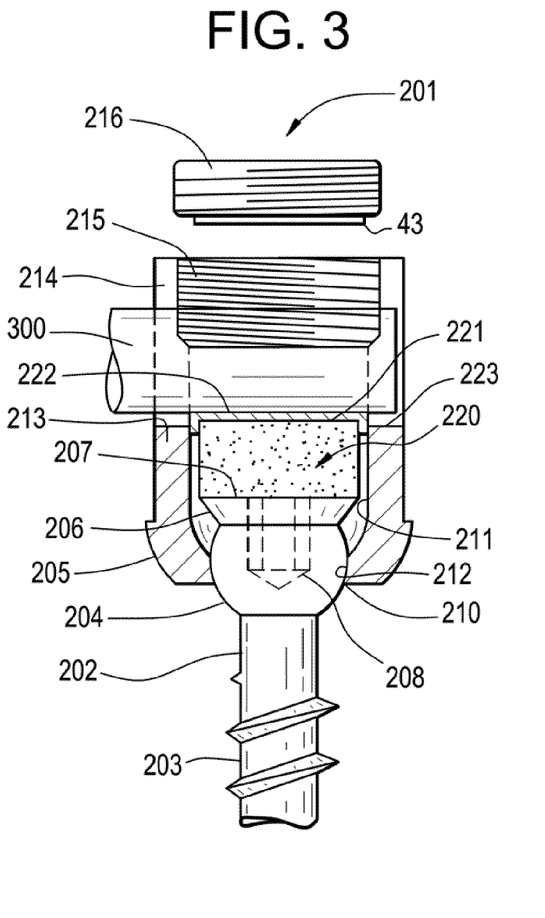
FIG. 3 shows an illustration in partial section of an embodiment of the anchoring device in the unloaded state.
Figure 4:
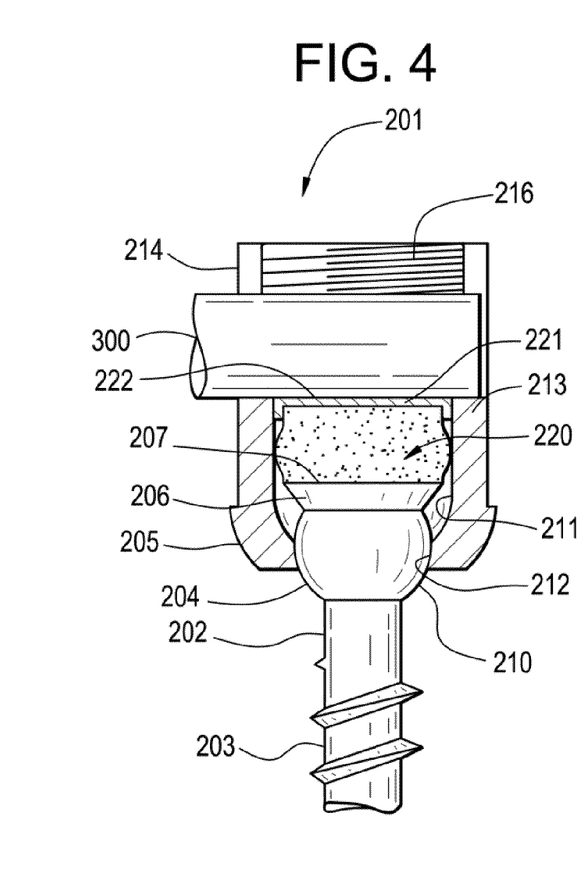
FIG. 4 shows an illustration in partial section of an anchoring device in the loaded state in the resting position.
Figure 5:
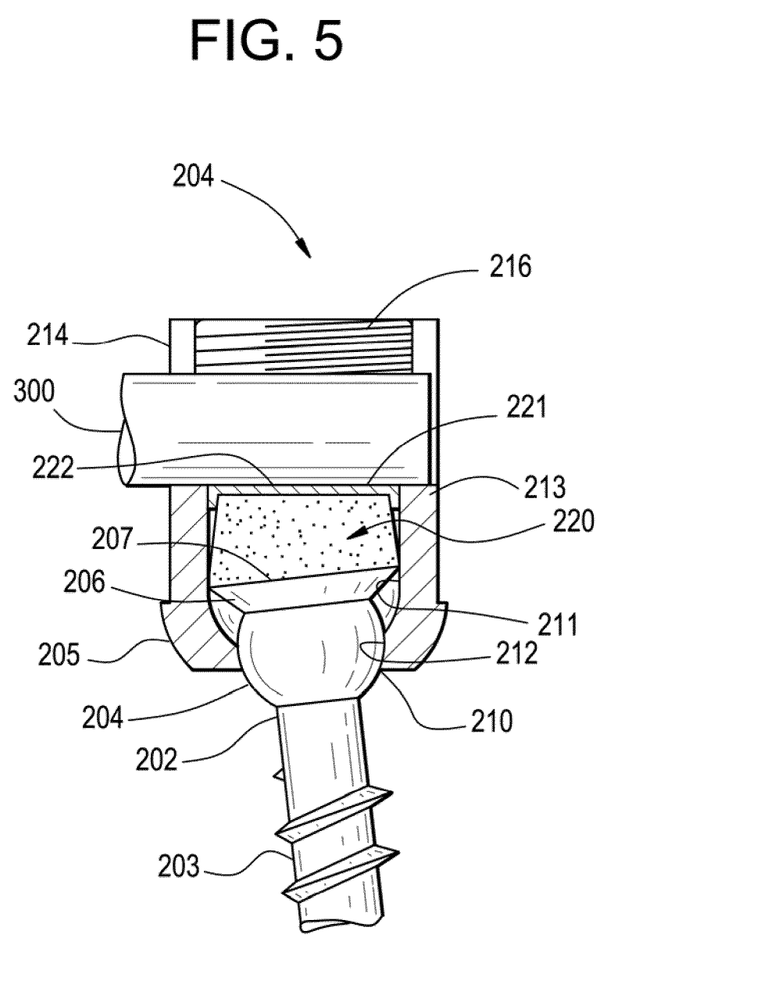
FIG. 5 shows an illustration in partial section of an anchoring device in the loaded state during the action of a force upon the anchoring element.

Now referring to FIGS. 3-5, in some embodiments of the present invention, flexible rods 300 of the present invention are combined with a pair of dynamic anchoring devices 201. Preferably, each of these dynamic anchoring devices comprises i) a shank 203 for anchoring into a bone or a vertebra, ii) a head connected to the shank, iii) a receiving part (or "housing") 205 for the head and iv) a motion-providing bearing element 220 acting on the head. The bearing element is formed and located in such a way that, upon a movement of the element from a first angular position of the shank relative to the receiving part into a second angular position, the rod stiffness provides a restoring force that forces the head to pivot. Accordingly, the present invention includes a dynamic stabilization device, in particular for vertebrae. In such a stabilization device, the flexible rod is connected to two anchoring devices. At least one of the anchoring devices is constructed as a dynamic anchoring element.

Therefore, the present invention provides an anchoring device comprising a screw element having a shank for anchoring in a bone or a vertebra and a head connected to the shank, a receiving part for receiving the head, and a motion-providing bearing element acting on the head, so that upon a movement of the motion providing bearing element from a first angular position of the shank relative to said receiving part into a second angular position, the rod flexibility urges the head to move.

Preferably, the motion providing bearing element acts on the side of the head facing away from the shank and is formed of a metal, ceramic or UHMWPE material.

Preferably, the head comprises a flat surface on the side facing away from the shank and the resilient pressure element comprises a flat surface cooperating therewith. The head may comprise a spherical segment-shaped section adjacent to the shank and a collar on the side facing away from the shank. Preferably, the head and the shank are separate parts, wherein the head has a central axis and the shank is connectable to the head at a predetermined angle α to the central axis.

Preferably, the receiving part comprises a support surface to support the head, the support surface and/or the head being polished or coated to reduce friction.

Preferably, the receiving part comprises a U-shaped recess for inserting a rod and the bearing element is arranged between the head and the rod when the rod is inserted into the receiving part.

The invention also provides a dynamic stabilization device for bones, in particular for vertebrae, having at least two anchoring devices connected to a flexible polymer rod, wherein one of the anchoring devices is formed as the anchoring device described above.

Additionally, the invention provides a method for using the dynamic anchoring device and a method for stabilizing bones, in particular for stabilizing vertebrae, wherein the anchoring device is as described above.

As can be seen in particular from FIGS. 3-5, in accord with one embodiment of the invention, the dynamic anchoring element 201 is formed as a polyaxial screw. It comprises a screw element 202 with a threaded shank part 203 and a head 204 formed in one piece therewith and a receiving part 205. The head 204 is substantially formed in the shape of a segment of a sphere and has on its end opposite to the shank part 203 a widened edge or collar 206, so that a flat front face 207 is formed which has a diameter which is larger than the diameter of the spherical segment-shaped section of the head. A recess for bringing into engagement with a screwing-in tool is further formed in the front face 207.

The receiving part 205 is substantially formed as cylindrically symmetric and has on one of its ends a coaxial first bore 210 the diameter of which is larger than that of the threaded section of the shank 203 and smaller than the spherical diameter of the spherical segment-shaped section of the head 204. It further has a coaxial second bore 211 which is open at the end opposite the first bore 210 and the diameter of which is large enough for the screw element 202 to be inserted through the open end with its threaded section through the first bore 210 and with the spherical segment-shaped section of the head 204 to the bottom of the second bore. In the receiving part, adjacent to the first bore 210 a section 212 is provided, shaped like a segment of a hollow sphere, the radius of which is substantially identical to the radius of the section of the spherical segment-shaped head 204. The receiving part further has a U-shaped recess 213, extending from the open end towards the first bore 210, the bottom of which is directed towards the first bore 210 and by which two open legs 214 are formed, only one of which is illustrated in the figures. An inner thread 215 is formed in the receiving part adjacent to the open end of the legs 214. The width of the U-shaped recess 213 is minimally larger than the diameter of a rod 300 to be received therein which connects several such polyaxial screws. The depth of the U-shaped recess is dimensioned in such a way that when the rod is inserted a fixing screw 216 can be screwed in between the legs. The set screw 216 is shown having a low friction rod contacting surface 43.

The section 212 of the receiving part which is shaped like a segment of a hollow sphere is preferably polished smooth or coated with a material which increases the sliding capacity, so the head 204 can easily be swiveled in the section 212 of the receiving part. Alternatively, or additionally the head 204 is polished smooth or coated.

Between the inserted rod 300 and the head 204 of the screw element, a motion-providing bearing element 220 is provided. The bearing element 220 is formed in the shape of a cylinder and has a diameter which is smaller than the inner diameter of the second bore 211 of the receiving part and which is preferably identical to the diameter of the front face 207 of the head. The axial length of the bearing element 220 runs the full length of the head and sometimes therebeyond (i.e., is slightly larger than or identical to the distance between the front face 207 of the head 204 and the bottom of the U-shaped recess 213 in the inserted state). The upper surface of the bearing element is a low friction surface to allow for translation of the rod and/or pivoting of the head in response to physiologic motion.

Between the bearing element 220 and the inserted rod 300 a cap 221 is provided, which covers the bearing element on the side facing the rod and which is constructed from an inflexible material, for example a synthetic material or a body-compatible metal. The outer diameter of the cap 221 is dimensioned in such a way that the cap is displaceable by sliding in the second bore of the receiving part and the inner diameter of the cap substantially corresponds to the outer diameter of the bearing element 220 when this is in an unloaded state.

FIG. 3 shows the unloaded state in which the screw element 202, the bearing element 220 and the cap 221 are inserted into the receiving part and the rod 300 is placed into the U-shaped recess 213, but the inner screw has not yet been screwed down. In this state, the side 222 of the cap 221 facing away from the pressure element 213 is at a slightly higher position than the bottom of the U-shaped recess 213, so that the rod rests with its lower side on the surface 222 of the cap and thus a gap 213 is formed between the lower side of the rod and the bottom of the U-shaped recess 213.

In operation, as shown in FIG. 3, first the screw element 202 is inserted into the receiving part 205 from the open end thereof until the head rests against the section 212 of the receiving part shaped like a segment of a hollow sphere. The screw element is then screwed into the vertebra. Then, the bearing element 220 together with the cap 221 placed thereon is inserted into the receiving part, the receiving part is aligned and the rod inserted. Finally, the inner screw 216 is screwed into the receiving part.

As illustrated in FIG. 4, the inner screw is screwed in until it presses the rod against the bottom of the U-shaped recess and thus fixes the rod. At the same time, the rod presses on the cap 221, which serves for even distribution of the force of pressure exerted by the rod on to the entire surface of the pressure element. In the state shown in FIG. 4, the bearing element 220 is under bias in respect of the screw head 204 and, due to the return force, it presses with its lower side evenly on the front face 207 of the head. In this way, the head is pressed against the section 212 of the receiving part.

The screw element 202 screwed into the vertebral body is moved out of its resting position by a self-movement of the vertebral column. When the vertebra moves towards the rod at an angle of 90° to the rod axis there is uniform compression of the pressure element and the angle of the shank relative to the receiving part does not change. When the vertebra moves at an angle other than 90° to the rod axis, as shown in FIG. 5, there is a swiveling of the head, which easily slides into section 212 of the receiving part. Thereby, the front face 207 of the screw head exerts a compression force upon the pressure element on one side which compresses it on one side near the edge. On the other hand, on the opposite side, the pressure element standing under pre-stress expands owing to the relief of pressure. Thus, the pressure element always remains in contact with the screw head.

The swivel range can also or additionally be set by the selection of the diameter of the collar 206 of the screw head relative to the diameter of the second bore 211 of the receiving part. When the collar 206 abuts on the wall of the receiving part in the swiveled position of the screw element 202, no further swiveling is possible.

Figure 6A:
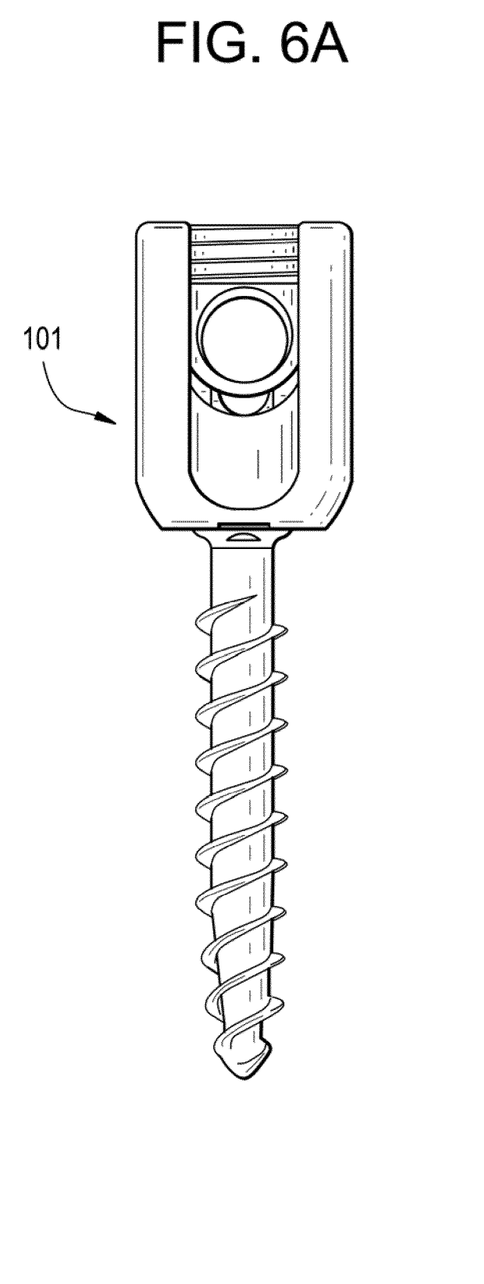
FIG. 6a discloses a mobile anchor of the present invention that slides upon the rod without pivoting.
Figure 6B:
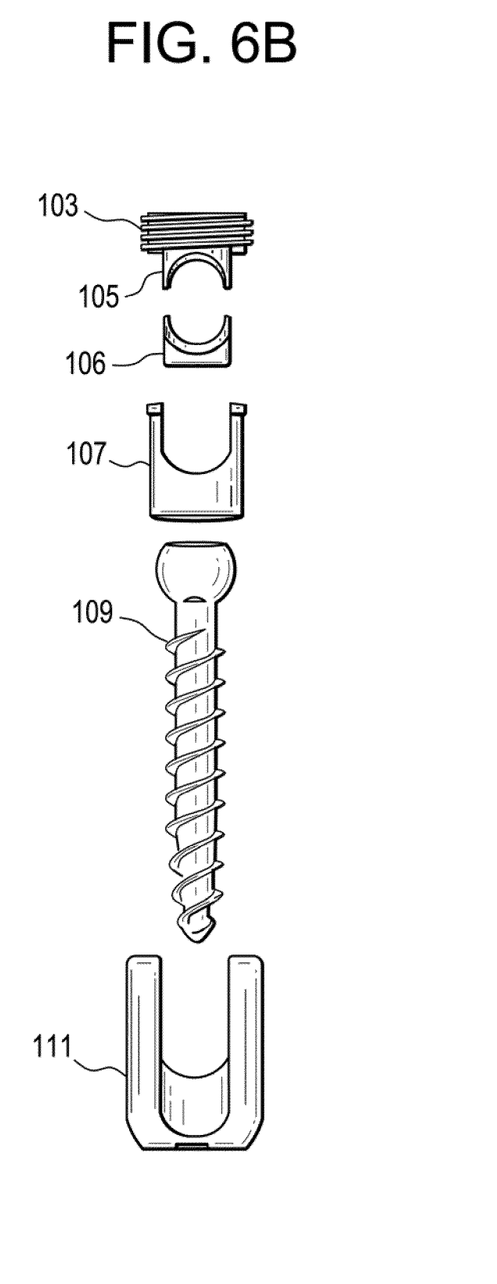
FIG. 6b discloses the anchor of FIG. 6a as an exploded assembly.

FIG. 6a discloses an additional anchor 111 of the present invention that slides upon the rod without pivoting. FIG. 6b discloses the anchor of FIG. 6a as an exploded assembly comprising:
   a) a conventional polyaxial head housing 111 having a throughbore (not shown),
   b) a conventional screw 109 having a head and a shank, the shank passing through the throughbore of the housing so that the head sets in the housing,
   c) a conventional locking cap 107 adapted to apply axial pressure to screw head, thereby locking the shank with respect to a rod,
   d) lower bearing 106 seated within the locking cap and having a surface adapted for receiving a rod, the surface possessing a low friction face that reduces wear generation,
   e) a set screw 103 adapted to seat in the head housing to lock the rod thereto, the set screw comprising a low friction, upper bearing surface 105 for bearing upon the rod and reducing wear generation.

The non-pivoting device of FIGS. 6a and 6b can be suitably used as a PDS device for treating degenerative disc disease (DDD), stenosis, and degenerative spondylolisthesis. It may also be used in protective capacity for topping off applications in an effort to prevent adjacent disc disease. Therefore, in accordance with the present invention, there is provided a method of treating a spine while allowing physiologic or near-physiologic motions, comprising the steps of:
   i) attaching to the spine of a patient having a degenerated disc a posterior dynamic spinal stabilization system comprising:
      a) a rod having a first end and a second end,
      b) a mobile anchor having i) a shank and ii) a rod-receiving portion mated to the first end of the rod, wherein the rod-receiving portion translates along the rod,
      c) a fixed anchor having i) a shank and ii) a rod-receiving portion locked to the second end of the rod,
   wherein the shank of the mobile anchor is attached to a first vertebra, and the shank of the fixed anchor is attached to the second vertebra.

In preferred embodiments thereof, the rod receiving portion of the mobile anchor is adapted to pivot about the rod.

Figure 7A:
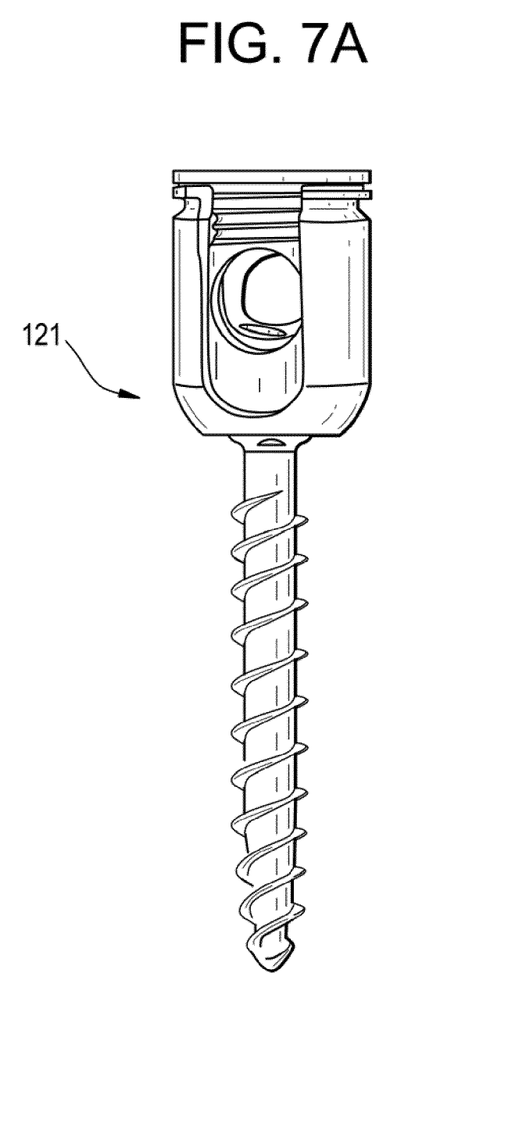
FIG. 7a discloses a mobile anchor of the present invention in which the screw not only slides upon the rod, but it also pivots.
Figure 7B:
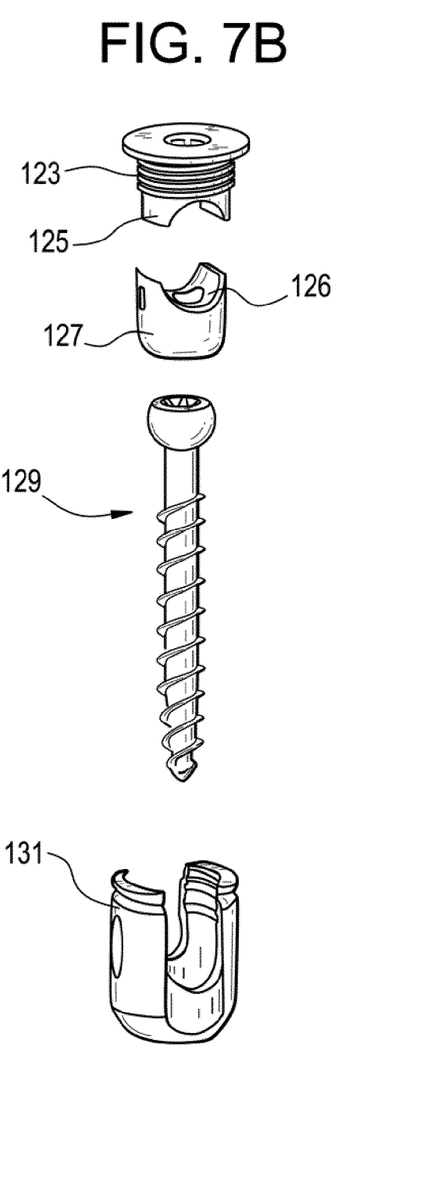
FIG. 7b discloses the anchor of FIG. 7a as an exploded assembly.

FIG. 7a discloses a mobile anchor 121 of the present invention in which the screw not only slides upon the rod, but it also pivots. FIG. 7b discloses an exploded assembly comprising:
a) standard polyaxial head 131 having a throughbore (not shown);
b) a conventional screw 129 having a head and a shank, the shank passing through the throughbore of the housing
c) a locking cap 127 adapted to apply axial pressure to screw head, thereby locking the shank with respect to the rod, the cap comprising a low friction, lower bearing surface 126 for the rod,
d) a set screw 123 adapted to seat in the head housing to lock the rod thereto, the set screw comprising a low friction, upper bearing surface 125 for bearing upon the rod.

In some embodiments of the present invention, the anchor is adapted to translate along the rod by providing the screw with low friction surfaces that contact the rod. Preferably, this would entail using both a low friction, motion-providing bearing element and a low friction set screw. In some embodiments, each of these low friction surfaces comprises a material selected from the group of a polymer, a ceramic and a metal. Preferably, it is a polymer.

The stops of the present invention may include any conventional component placed on the rod adjacent to the mobile anchor in order to limit the translation of the anchor along the rod. The stop may attach to a single rod, or attach to a pair of bilateral rods thereby acting as a cross-connector. The stop may be desirably spaced from the anchor so that the preferred amount of anchor translation along the rod is between 0.5 mm and 12 mm. In preferred embodiments, the stop is a bumper-stop and may be fabricated by using a metallic stop 71 with an anchor-limiting surface 73 made from a polymer or elastomer component. The polymer or elastomer may be slid onto the collar as a separate component or it may be overmolded. In addition, the elastomer component may have a geometry that would cause it to perform like a cushioning stop, i.e. a bumper with flexible struts, sponge-like. The stop may be integral to the rod, or may be a secondary component attached to the rod to create a stop. The surgeon may position the stops at distances from the mobile anchor that are considered to produce the desired limited amount of motion.

The spinal rod of the present invention may be a rod conventionally used in the spinal stabilization field. The present invention can be used with either a rigid rod (such as titanium or stainless steel) or a flexible rod (such as polymer, spring or composite) that allows bending and translation of the vertebral bodies relative to one another. The rod has a preferred diameter within the range of 1.0 to 8.0 mm, and may more preferably be about 5.5 mm. The rod may have a constant cross section or a tapered cross section. For example, it may form a ramp that makes motion increasingly difficult as the mobile anchor translates along the rod. In another embodiment, a plurality of polymer rods could be provided with varying flexibilities. In this case, the inherent stiffness of each rod will dictate the amount of bend it provides in vivo, and the bend will influence the anchor's ability to slide. In these cases, a relatively stiff rod may allow for less translation than a more flexible rod. In some embodiments, the metal or polymer rod carries a polymer sleeve that is free to slide along the rod, thereby limiting motion. In some preferred embodiments, the rod is a polymer rod.

Although many embodiments of the present invention use a polyaxial screw that is adapted to pivot, in some alternative embodiments, a conventional polyaxial screw may be provided that would allow the angle of the shank to be locked relative to the polyaxial head. The set screw component of the anchor contains two useful surfaces—a first that applies pressure radially to the cap (receiving part) and a second that applies pressure axially to the rod. Similarly, the cap contains a first surface that interfaces with the rod and a second that interfaces with the set screw. As the set screw is tightened, the rod is sandwiched between the polymeric surface on the set screw and the head of the shank. The polymeric inserts that are disposed between the spherical head of the shank and the rod can be made from any biocompatible low friction wear surface. The shank of either the mobile anchor or the fixed anchor may be adapted to allow pivoting motion. Alternatively, it may remain fixed.

In some embodiments (not shown), the rod is fitted with at least one polymeric sleeve. In these embodiments, the surgeon inserts the rod, passes the sleeve over the rod, and aligns the sleeves with the caps of adjacent bone anchors before tightening the sleeves within the caps. Such a sleeve not only provides a bearing surface within the bone anchor to prevent metal-on-metal contact, it also allows for some free sliding motion of the anchor along the rod.

In some embodiments, a construct may be fabricated using a plurality of anchors (along with the corresponding stops) sufficient to treat multiple levels in order to tailor and transition motion, such that a motion gradient is achieved.

One skilled in the art will appreciate that the rod of the device may be configured for use with any type of bone anchor, e.g., bone screw or hook; mono-axial or polyaxial. Typically, a bone anchor assembly includes a bone screw, such as a pedicle screw, having a proximal head and a distal bone-engaging portion, which may be an externally threaded screw shank. The bone screw assembly may also have a receiving member that is configured to receive and couple a spinal fixation element, such as a spinal rod or spinal plate, to the bone anchor assembly.

The receiving member may be coupled to the bone anchor in any well-known conventional manner. For example, the bone anchor assembly may be poly-axial, as in the present exemplary embodiment in which the bone anchor may be adjustable to multiple angles relative to the receiving member, or the bone anchor assembly may be mono-axial, e.g., the bone anchor is fixed relative to the receiving member. An exemplary poly-axial bone screw is described U.S. Pat. No. 5,672,176, the specification of which is incorporated herein by reference in its entirety. In mono-axial embodiments, the bone anchor and the receiving member may be coaxial or may be oriented at angle with respect to one another. In poly-axial embodiments, the bone anchor may be biased to a particular angle or range of angles to provide a favored angle to the bone anchor. Exemplary favored-angle bone screws are described in U.S. Patent Application Publication No. 2003/0055426 and U.S. Patent Application Publication No. 2002/0058942, the specifications of which are incorporated herein by reference in their entireties.

In some embodiments of the present invention, the rod-receiving portion of the device comprises inner and outer portions made of distinct materials. Each of these portions is designed to carry out one of the two primary functions of the rod-receiving portion: 1) attaching to the remainder of the mobile anchor and 2) sliding upon the rod. In these embodiments, the inner portion of the rod-receiving portion is made of a low friction material (preferably, a polymer) to allow limited sliding upon the rod therein. In contrast, the outer portion of the rod-receiving portion is made of a high stiffness material (such as a metal) in order to provide secure locking of the rod-receiving portion to the other components of the device.

In some embodiments, the lower part of the set screw functions as the upper bearing component of the rod-receiving portion. In these embodiments, the set screw can be made of two components having dissimilar materials. Preferably, the set screw can comprise: a) a lower polymer portion functioning as the low friction, upper bearing component of the rod-receiving portion, and b) an upper metallic or ceramic threaded portion whose high stiffness allows its locking to the mobile anchor housing.

Likewise, in some embodiments, the upper part of the locking cap may function as the lower bearing component of the rod-receiving portion. In these embodiments, the locking cap can be made of two components having dissimilar materials. Preferably, the locking cap can comprise a) an upper polymer portion functioning as the low friction, lower bearing component of the rod-receiving portion, and b) a lower metallic or ceramic backing that seats on the screw head.

In some embodiments, a separate component termed a "sliding bearing" can be used in the device of the present invention. The "sliding bearing" is a sleeve component that wraps around the rod within the mobile anchor housing. Accordingly, an upper portion of this sleeve is interpositioned between the set screw and the rod, and a lower portion of this sleeve is interpositioned between the locking cap and the rod. The sliding bearing can be composed of i) an inner polymer sleeve functioning as the low friction bearing surface and ii) an outer metal sleeve whose high stiffness allows a set screw or locking cap to clamp it. The metallic feature of this hybrid sleeve component desirably prevents compression of its polymer bearing feature, which may undesirably hinder motion.

In the embodiments described above, it is generally preferably that the spinal rod be made of a polymer (such as PEEK) in order to provide a certain amount of flexibility desirable for posterior dynamic stabilization and to accommodate limited sliding of the mobile anchor thereon.

Figure 8:
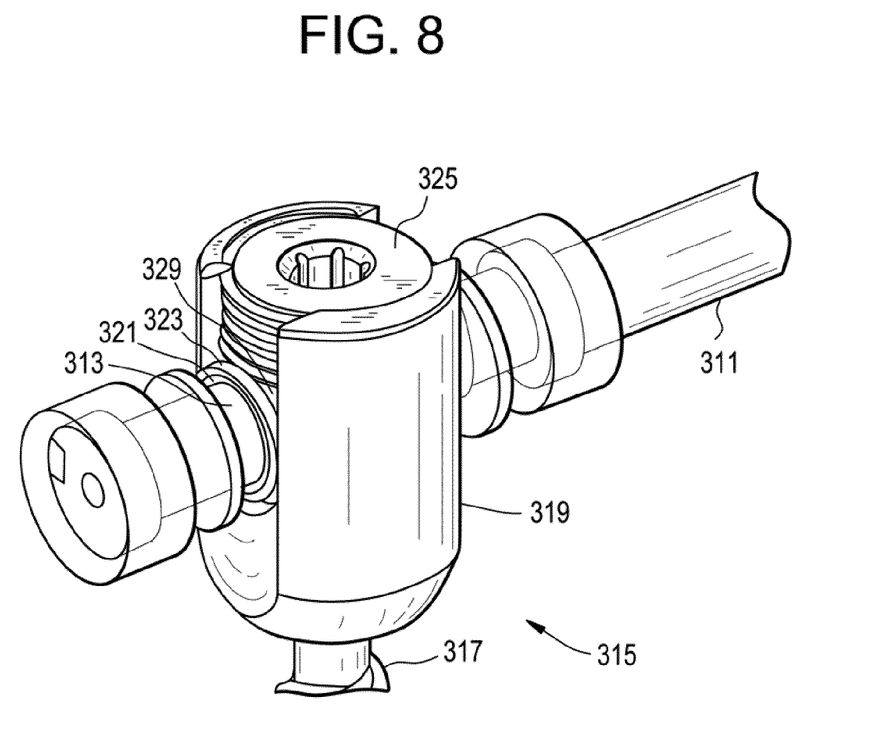
FIG. 8 discloses a screw of the present invention attached to a rod, wherein the screw has a sleeve having an upper polymer portion and a lower metallic portion.

Therefore, in accordance with the present invention, and now referring to FIG. 8, there is provided a posterior dynamic spinal stabilization system comprising:
   a) a spinal rod 311 having a first end portion 313 and a second end portion,
   b) a mobile anchor 315 having i) a shank 317 and ii) a rod-receiving portion 319 mated to the first end portion of the rod, wherein the rod-receiving portion translates along the rod,
   c) a fixed anchor having i) a shank and ii) a rod-receiving portion locked to the second end portion of the rod,
wherein an inner portion 321 of the rod-receiving portion of the mobile anchor comprises a polymer allowing limited motion of the mobile anchor on the rod, and
wherein an outer portion 323 of the rod-receiving portion of the mobile anchor comprises a high stiffness material (such as a metal) securing locking of the rod-receiving portion.

Preferably, this system further comprises d) a set screw 325 housed within the mobile anchor and bearing against the rod, wherein a lower part of the set screw comprises an upper bearing component of the rod-receiving portion.

In some embodiments, the set screw of this sliding bearing system comprises a) a polymer portion comprising the upper bearing component of the rod receiving portion, and b) a metallic or ceramic threaded portion securing the set screw to the mobile anchor. Preferably, the polymer portion comprises PEEK.

In other embodiments, this sliding bearing system further comprises:
   d) a set screw secured to the mobile anchor,
wherein the rod-receiving portion comprises a sliding bearing sleeve 329 wrapped around the rod, wherein the sliding bearing sleeve comprises an inner polymer component bearing against the rod and a metal outer surface contacting the set screw. Preferably, the inner polymer component comprises PEEK.

In other embodiments, this sliding bearing system further comprises:
   d) a locking cap as a lower bearing component of the rod receiving portion.

Preferably, this locking cap comprises a) an upper polymer portion functioning as the lower bearing component, and b) a metallic or ceramic backing that seats on the shank. Preferably, the upper polymer portion comprises PEEK, and the rod comprises a polymer such as PEEK.

In some embodiments, the rod-receiving portion that acts as a sliding bearing has a substantially spherical outer surface. The spherical bearing is adapted to allow:
   a) sliding of the rod through the center of the spherical bearing, and
   b) rotation of the spherical bearing within the device to allow toggling/pivoting while preventing torque transmission to screw-bone interface.

Figure 9A:
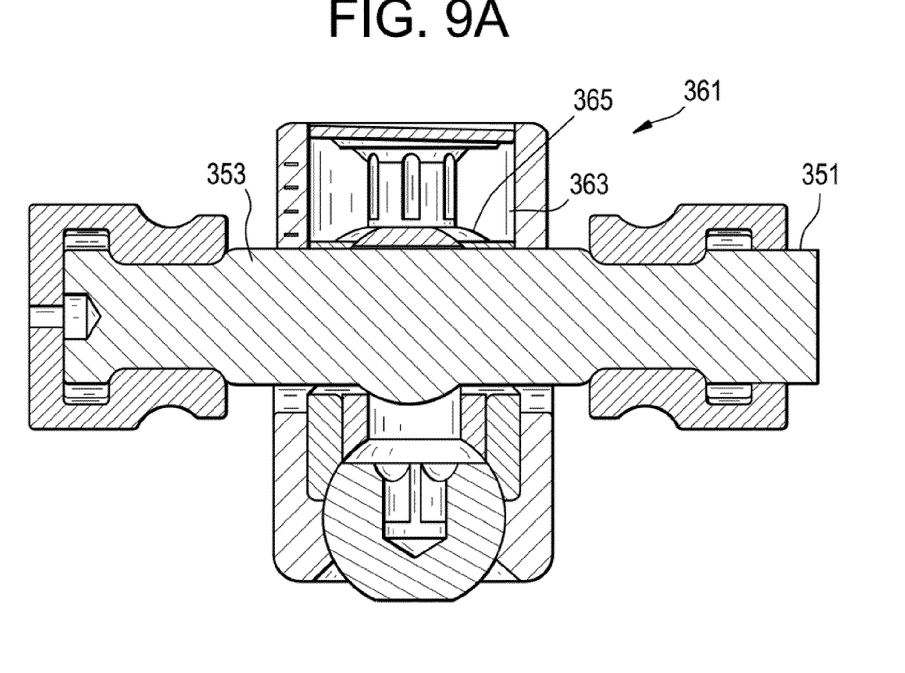
FIG. 9a is a cross section of a mobile screw-rod assembly wherein the screw has a spherical bearing surface.
Figure 9B:
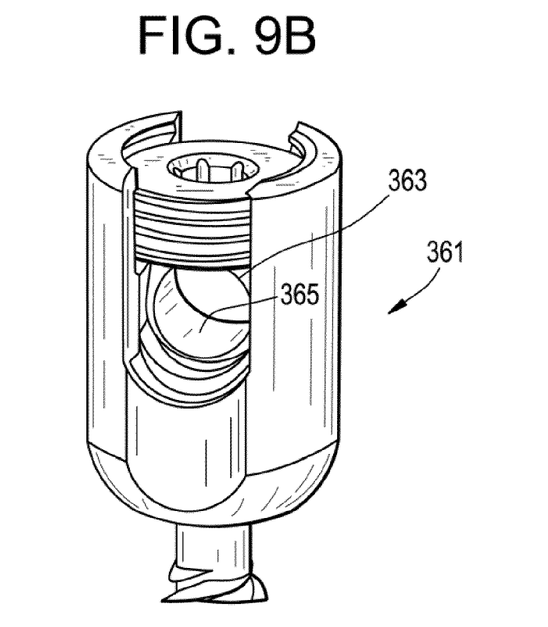
FIG. 9b is a mobile screw having a spherical bearing surface.

Therefore, in accordance with the present invention, and now referring to FIGS. 9a and 9b, there is provided a posterior dynamic spinal stabilization system comprising:
   a) a rod 351 having a first end portion 353 and a second end portion,
   b) a mobile anchor 361 having i) a shank and ii) a rod-receiving portion 363 mated to the first end portion of the rod, wherein the rod-receiving portion translates along the rod,
   c) a fixed anchor having i) a shank and ii) a rod-receiving portion locked to the second end portion of the rod,
wherein the rod receiving portion of the mobile anchor has a substantially spherical outer surface 365.

In the spherical sliding bearing embodiments, the rod preferably comprises a polymer such as PEEK.

In some spherical sliding bearing embodiments, the rod-receiving portion of the mobile anchor has an inner surface adapted to contact the rod, wherein the inner surface comprises a polymer (such as PEEK).

In some spherical sliding bearing embodiments, the substantially spherical outer surface is adapted to allow pivoting of the mobile anchor about the rod.

In some embodiments, there is provided a polymeric bumper/stop component (or sleeve) located between adjacent pedicle screws that is adapted to float on the rod. The purpose of this polymeric sleeve is to provide a soft stop that limits the translation of the mobile anchor. The use of such a bumper obviates the need for employing fixed stops, thereby reducing inventory and simplifying the surgical procedure. The difference between the pedicle screw spacing and the length of the bumper of this embodiment defines a gap, which determines the amount of mobile anchor translation freely allowed along the rod. In these embodiments, the system provides a first region of free travel defined by the gap and then a second region of increasing resistance provided by the polymeric sleeve.

Figure 10:
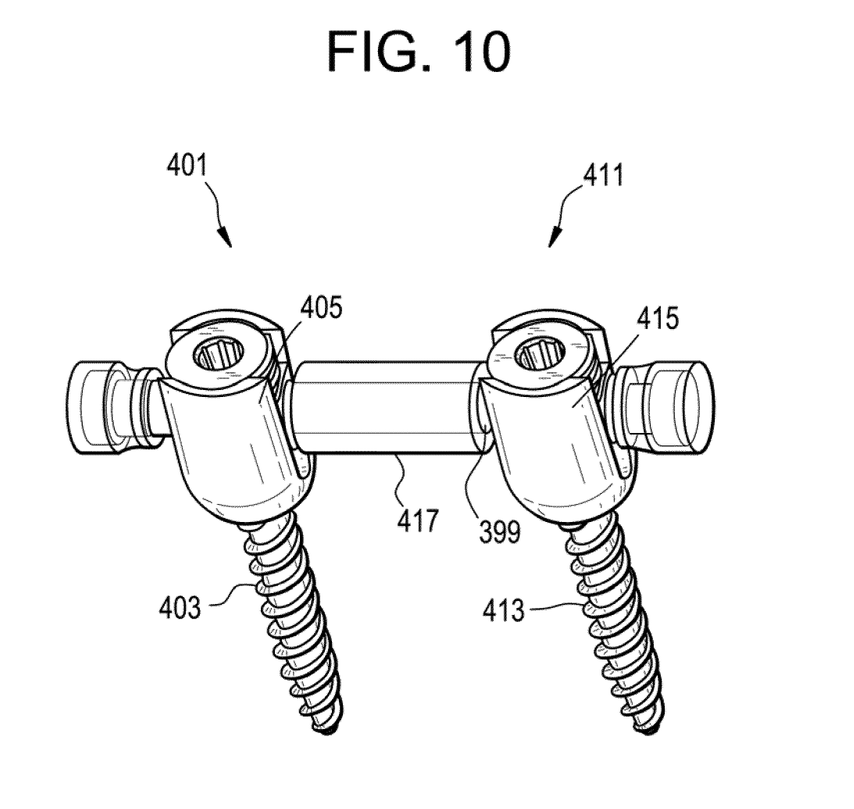
FIG. 10 discloses an assembly having a polymer screw disposed between two screws.

Therefore, in accordance with the present invention, and now referring to FIG. 10, there is provided a posterior dynamic spinal stabilization system, comprising:
   a) a rod 399 having a first end portion and a second end portion,
   b) a mobile anchor 401 having i) a shank 403 and ii) a rod-receiving portion 405 mated to the first end portion of the rod, wherein the rod-receiving portion translates along the rod, c) a fixed anchor 411 having i) a shank 413 and ii) a rod-receiving portion 415 locked to the second end portion of the rod, d) a polymeric sleeve 417 received upon the rod at a location between the mobile anchor and the fixed anchor.

In some embodiments, thereof, the polymeric sleeve comprises PEEK.

In some polymer sleeve embodiments, the rod comprises a polymer (such as PEEK).

In some polymer sleeve embodiments, the location of the sleeve defines a first gap along the rod between the sleeve and the mobile anchor, and preferably the polymeric sleeve floats upon the rod.

In some embodiments, the locking cap of the present invention is a hybrid component comprising i) a lower metallic component adapted to apply axial pressure to the screw head, thereby locking the shank with respect to the housing, and ii) an upper polymer bearing surface for sliding upon the rod.

Therefore, in accordance with the present invention, there is provided a dynamic spinal stabilization system, comprising:
 a) a spinal rod having a first end portion and a second end portion,
 b) a polyaxial head housing having a throughbore;
 c) a screw having a head and a shank, the shank passing through the throughbore of the housing;
 d) a locking cap comprising i) a lower metallic component adapted to apply axial pressure to the screw head, thereby locking the shank with respect to the housing, and ii) an upper polymer bearing surface for sliding upon the rod, and
 e) a set screw seated in the head housing to bear against the rod, the set screw comprising a low friction, upper bearing surface for sliding upon the rod.

In some of these hybrid locking cap embodiments, the spinal rod comprises a polymer (such as PEEK).

In some of the hybrid locking cap embodiments, the polymer bearing surface of the locking cap comprises PEEK.

In some embodiments, the set screw is a hybrid component comprising i) an upper metallic component seated in the head housing to lock the rod thereto, and ii) a lower polymeric upper bearing surface for sliding upon the rod. Therefore, in accordance with the present invention, there is provided a dynamic spinal stabilization system, comprising:
 a) a spinal rod having a first end portion and a second end portion,
 b) a polyaxial head housing having a throughbore;
 c) a screw having a head and a shank, the shank passing through the throughbore of the housing;
 d) a locking cap adapted to apply axial pressure to the screw head, thereby locking the shank with respect to the rod, the cap comprising a low friction, lower bearing surface for sliding upon the rod, and
 e) a set screw comprising i) an upper metallic component seated in the head housing to lock the rod thereto, and ii) a lower polymeric upper bearing surface bearing upon the rod.

In some of these hybrid set screw embodiments, the spinal rod comprises a polymer (such as PEEK).

In some of the hybrid set screw embodiments, the polymeric bearing surface of the set screw comprises PEEK.

In some embodiments, the assembly may be implanted in accordance with the minimally invasive techniques and instruments disclosed in U.S. Pat. No. 7,179,261; and US Patent Publication Nos. US2005/0131421; US2005/0131422; US 2005/0215999; US2006/0149291; US2005/0154389; US2007/0233097; and US2005/0192589, the specifications of which are hereby incorporated by reference in their entireties. In FIG. 1c, an MIS attachment feature located at an end of the rod is shown.

The material of construction for a rod used in accordance with the present invention may be selected from any biocompatible material, such as a polymer, titanium alloy, stainless steel, and a composite. The preferred surface finish on the contact surfaces of the metallic components will be within the range of Ra 0.02 to Ra 0.5 μm, preferably within the range of Ra 0.02 to Ra 0.15 μm.

The rod and stop components of the design may be made from biocompatible, implantable materials known in the art such as stainless steel, titanium, Nitinol, polyetheretherketone (PEEK) or alternative polyarylketones, carbon fiber reinforced polymers. The bumpers may be selected from high performance elastomers such as silicones, dimethylsiloxanes, silicone-urethanes, polyether-urethanes, silicone-polyether-urethanes, polycarbonate urethanes, and silicone-polycarbonate-urethanes.

Preferably, the rod, shank, cap and stop components are titanium alloy (Ti-6Al-4V) or cobalt-chrome alloy (e.g. Co—Cr—Mo). If a cobalt-chrome alloy is selected, the alloy is preferably in a work-hardened condition so as to resist deformation upon securing to the bone anchor (e.g with a set screw). Preferably, the solid rod component may be either titanium alloy or PEEK.

If a metal is chosen as a material of construction, then the metal is preferably selected from the group consisting of nitinol, titanium, titanium alloys (such as Ti-6Al-4V), cobalt-chrome alloys (such as CrCo or Cr—Co—Mo) and stainless steel.

If a polymer is chosen as a material of construction, then the polymer is preferably selected from the group consisting of CFRP, polycarbonates, polyesters, (particularly aromatic esters such as polyalkylene terephthalates, polyamides; polyalkenes; poly(vinyl fluoride); PTFE; polyarylethyl ketone PAEK; and mixtures thereof.

In some embodiments, the solid rod component is made from a composite comprising carbon fiber. Composites comprising carbon fiber are advantageous in that they typically have a strength and stiffness that is superior to neat polymer materials such as a polyarylethyl ketone PAEK. In some embodiments, the tube is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
 a) 40-99% (more preferably, 60-80 vol %) polyarylethyl ketone (PAEK), and
 b) 1-60% (more preferably, 20-40 vol %) carbon fiber, wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

The elastomer bumper component is preferably made of a thermoplastic, biocompatible, high performance polycarbonate-urethane (PCU). The stiffness, or durometer of the PCU can be tailored to meet the specifications for the dynamic device. In preferred embodiments, the surface of the device components that will be attached to the elastomer bumper are treated prior to attaching the bumper using known surface treatment methods such as surface roughening (e.g. grit blasting), chemical functionalization (e.g. primers), and plasma treatments know in the art. Alternatively or in conjunction with using a surface treatment, an adhesive may be used to enhance bonding, e.g. using cyanoacrylates. In one preferred embodiment, the surfaces of the device components that will be attached to the elastomer bumper will first be roughened using grit blasting, then chemically functionalized using primer, then the elastomer will be overmolded onto the device components.

I claim:

1. A posterior dynamic spinal stabilization system comprising:
   a) a rod having a first end and a second end,
   b) a mobile anchor having i) a shank and ii) a rod-receiving portion mated to the first end of the rod, wherein the rod-receiving portion is adapted to translate along the rod and pivot about the shank, the mobile anchor adapted for translation and pivoting along the rod after implantation,
   c) a fixed anchor having i) a shank and ii) a rod-receiving portion locked to the second end of the rod, the fixed anchor adapted to lock to the second end of the rod after implantation, and
   d) a first motion limiting stop positioned on the rod at a location cranial to the mobile anchor,
   e) a set screw adapted to seat in the rod-receiving portion of the mobile anchor, the set screw comprising a low friction, upper bearing surface for bearing upon the rod and reducing wear generation, and
   f) lower bearing seated within the rod-receiving portion of the mobile anchor and having a surface adapted for receiving a rod, the surface possessing a low friction face that reduces wear generation,
wherein the low friction surface of the lower bearing has an arcuate contact surface adapted for contacting the rod.

2. The system of claim 1 wherein the device further comprises:
   e) a second motion limiting stop positioned on the rod at a location caudal to the mobile anchor.

3. The system of claim 2 wherein the first or second motion limiting stop comprises a polymeric bumper.

4. The system of claim 1 wherein the shank of the mobile anchor is fixed.

5. The system of claim 1 wherein the shank of the mobile anchor is adapted to allow pivoting motion.

6. The system of claim 1 wherein the shank of the fixed anchor is fixed.

7. The system of claim 1 wherein the rod is a polymer rod.

8. The system of claim 1 wherein mobile anchor comprises i) a shank forming a head, and ii) a bearing element acting on the head and disposed between the head and the rod.

9. The system of claim 1 further comprising:
   d) a polymeric sleeve carried on the rod.

10. The system of claim 1 wherein the rod is rigid.

11. The system of claim 1 wherein the rod is flexible.

12. The system of claim 1 wherein the low friction, upper bearing surface of the set screw has an arcuate contact surface adapted for contacting the rod.

13. A posterior dynamic spinal stabilization system comprising:
   a) a rod having a first end and a second end,
   b) a mobile anchor having i) a shank and ii) a rod-receiving portion mated to the first end of the rod, wherein the rod-receiving portion is adapted to translate along the rod, the mobile anchor adapted for translation and pivoting along the rod after implantation,
   c) a fixed anchor having i) a shank and ii) a rod-receiving portion locked to the second end of the rod, the fixed anchor adapted to lock to the second end of the rod after implantation,
   d) a first motion-limiting stop positioned on the rod at a location caudal inferior to the mobile anchor and comprising a metallic collar and an elastic bumper,
   e) a set screw adapted to seat in the rod-receiving portion of the mobile anchor to lock the rod thereto, the set screw comprising a low friction, upper bearing surface for bearing upon the rod and reducing wear generation, and
   f) a lower bearing seated within the rod-receiving portion of the mobile anchor and having a surface adapted for receiving a rod, the surface possessing a low friction face that reduces wear generation, and
wherein the low friction surface of the lower bearing has an arcuate contact surface adapted for contacting the rod.

14. The system of claim 13 wherein the low friction, upper bearing surface of the set screw has an arcuate contact surface adapted for contacting the rod.

* * * * *